United States Patent [19]
Hu et al.

[11] Patent Number: 6,010,996
[45] Date of Patent: Jan. 4, 2000

[54] BIOCIDAL SURFACTANT COMPOSITIONS AND THEIR USE

[75] Inventors: Patrick C. Hu; Joe D. Sauer, both of Baton Rouge; Deborah A. Quebedeaux, Thibodaux; Conrad J. Langlois, Jr., New Roads, all of La.

[73] Assignee: Albemarle Corporation, Richmond, Va.

[21] Appl. No.: 09/164,713

[22] Filed: Oct. 1, 1998

[51] Int. Cl.⁷ ..................................................... C11D 1/65
[52] U.S. Cl. .......................................... 510/384; 510/427
[58] Field of Search ................................... 510/131, 132, 510/133, 384, 389, 427

[56] References Cited

U.S. PATENT DOCUMENTS

| | | | |
|---|---|---|---|
| 2,479,850 | 8/1949 | Marks | 167/22 |
| 3,997,453 | 12/1976 | Wixon | 252/8.75 |
| 4,091,113 | 5/1978 | Green et al. | 424/329 |
| 4,844,891 | 7/1989 | Rosen et al. | 424/76.4 |
| 4,847,089 | 7/1989 | Kramer et al. | 424/405 |
| 5,034,218 | 7/1991 | Duvel | 424/70 |
| 5,756,438 | 5/1998 | Rau et al. | 510/151 |

FOREIGN PATENT DOCUMENTS 200561  7/1990  Hungary.

OTHER PUBLICATIONS

Seymour S. Block, "Disinfection, Sterilization, and Preservation", 1991, Lea & Febiger publishers, Chapter 13 by John J. Merianos, "Quaternary Ammonium Antimicrobial Compounds", pp. 225–255.

Primary Examiner—Yogendra Gupta
Assistant Examiner—John R. Hardee
Attorney, Agent, or Firm—E.E. Spielman, Jr.

[57] ABSTRACT

A quaternary ammonium compound is combined with a water-soluble anionic surfactant having a hydrophile/lipophile balance (HLB) of 14 or above to form a biocidal/surfactant composition in which the amount of (ii) is up to 50 wt % of the total weight of these components. In the presence of water or other suitable aqueous media, such compositions appear to form a soluble charge complex. But whatever actually happens in the aqueous medium, the surfactant properties of the quaternary ammonium compound are improved without jeopardizing or impairing its germicidal properties.

32 Claims, 6 Drawing Sheets

0.1 WT% TOTAL ACTIVES
DOW CORNING HIGH VACUUM GREASE COATED GLASS SLIDE

FIG. I

BIOCIDAL SURFACTANT COMPOSITIONS AND THEIR USE

TECHNICAL FIELD

The invention relates to novel, efficacious biocidal cleaning compositions and their use.

BACKGROUND

Quaternary ammonium biocides (disinfectants) are well known and widely used. Unfortunately such materials suffer from a number of deficiencies resulting from their "cationic" nature. In particular, because they are highly susceptible to precipitation by a wide of variety of materials, such precipitation leads to removal and deactivation of the quaternary ammonium compound in a biocidal sense.

More particularly, quaternary ammonium biocides are precipitated from aqueous media and thus lose their effectiveness and are rendered inactive by a variety of organic "soils." Some of the soils are natural to the environment in which the disinfectant cleaner is to be used (blood serum, animal waste, fats, etc.). Some of the "soils" are in fact other ionic species, such as anionic surfactants, electrolytes, polyvalent ions, and similar materials. When deactivation occurs, the biocidal activity of the quaternary ammonium compound is dramatically diminished, even with organisms that the quaternary ammonium compound normally controls very readily such as gram positive bacteria.

This lack of activity in the case of quaternary ammonium biocides is well known and well documented with respect to particular pathological organisms, e.g., Mycobacterium tuberculosis, Hepatitis B virus, Polio Myelitis virus, and Canine Parvo virus. In order to compensate for these deficiencies, certain other "non-quaternary" biocides such as phenolic biocides, halogen-based biocides, etc., have been proposed for use with quaternary ammonium biocides.

Another deficiency of quaternary ammonium compounds is that their wetting and degreasing properties are less than desired. For example, cleaning products formulated with quaternary ammonium compounds often are not particularly effective when used on surfaces that are either porous or coated with an oily layer, or both. Indeed, among all surfactants, quaternary ammonium compounds are the poorest wetting agents. Also, they are generally poor emulsifiers. Moreover, due to adverse interaction with other surface actives, formulation of quaternary ammonium compounds is often impracticable.

Wetting is a very important attribute for any liquid products, especially when liquid formulations (e.g., products designed to kill germs on hard surfaces) need to penetrate into fine cracks or pores where shear force can not be adequately applied. Because of precipitation in the presence of conventional anionic surfactants, the options for surface tension reduction or better wetting properties are very limited. Although nonionic surfactants such as alcohol ethoxylates and ethoxylated alkylphenols can be used to enhance the wettability of quat-based liquid formulations, unfortunately the presence of nonionics adversely affect the germicidal efficiency of the quaternary ammonium compounds.

The cationic charge on quaternary ammonium compounds is responsible for their germicidal function. Unfortunately, however, undesirable deposit formation and buildup on hard surfaces is also attributable to the cationic charge of quaternary ammonium compounds. In particular, the positive charge tends to cause the quaternary ammonium compound to orient itself on the hard surface during application. As the carrying solvent evaporates, a hydrophobic surface can form, and this in turn can attract deposition thereon of greasy substances.

It would thus be of considerable advantage if a way could be found of improving the surfactant properties of quaternary ammonium compounds while at the same time not jeopardizing or impairing their germicidal properties. This invention is deemed to make possible the achievement of these objectives.

SUMMARY OF THE INVENTION

This invention provides a new approach for solving the foregoing deficiencies of quaternary ammonium biocides.

Pursuant to this invention (i) at least one quaternary ammonium compound, is combined with (ii) at least one water-soluble anionic surfactant having a hydrophile/lipophile balance (HLB) of 14 or above to form a biocidal/surfactant composition in which the amount of (ii) is up to 50 wt % of the total weight of (i) and (ii). Preferably the weight of (ii) is at least 1 wt % of the total weight of (i) and (ii). Particularly preferred proportions of (i) and (ii) are those wherein the weight of (ii) is in the range of about 2 to about 30 wt % of the total weight of (i) and (ii). The most preferred proportions are such that the weight of (ii) is in the range of about 5 to about 25 wt % of the total weight of (i) and (ii). In the presence of water or other suitable aqueous media, such compositions appear to form a soluble mosaic charge complex.

The compositions of this invention can be provided as solid compositions, e.g., as relatively small non-agglomerated solids such as powders, granules, flakes, and the like, or as larger agglomerated solids, such as bars, tablets, and the like. Alternatively, the compositions of this invention can be in the form of industrial water-based liquid cleaning/disinfecting concentrates formulated for dilution prior to use, or as more dilute finished cleaning/disinfecting compositions formulated for household usage.

By water-soluble is meant that each of components (i) and (ii) is soluble at least to the extent of 0.1% by weight in deionized water at 25° C. When used in forming an aqueous concentrate of this invention, each such component should have a water solubility of at least 1% by weight in deionized water at 25° C.

Another embodiment of this invention is a liquid cleaning/disinfecting composition formed by intimately mixing components (i) and (ii) above with water. In forming such compositions, components (i) and (ii) can be separately mixed with the water, or components (i) and (ii) can be mixed with the water as a preformed mixture and/or complex. In formulations for household usage, the total concentration of components (i) and (ii) proportioned as above, whether blended with the water separately or as a preformed mixture and/or complex, should be a cleansing and disinfecting quantity, which typically is in the range of about 0.1 to about 5 wt %, and preferably in the range of about 0.4 to about 1 wt %, based on the total weight of water plus components (i) and (ii). Industrial strength liquid formulations can contain any total amount of components (i) and (ii) that will dissolve in water at room temperature. Preferably, however, the amount used should not form a turbid solution at room temperature.

On the basis of the evidence available to date, and without being bound by theoretical considerations, it appears that in the presence of water one or more complexes are formed between the quaternary ammonium compound and the relatively small molecules of component (ii). In so doing, it appears that the anionic charge of these relatively small surfactant molecules increases the surface activity of the quaternary ammonium component of the complex through partial charge neutralization, a phenomenon which results in what can be termed a substance having a "mosaic charge." But whatever the mechanism, the result is that the product resulting from combining components (i) and (ii) in an aqueous medium exhibits better wetting and grease cutting properties than either component when used individually, while at the same time retaining the powerful biocidal (disinfectant) properties of the quaternary ammonium compound. Such synergistic behavior has been found to be surprisingly strong.

It is interesting to observe that the behavior of the low molecular weight anionics with relatively small molecular sizes used as component (ii) pursuant to this invention is different from the behavior of conventionally-used anionic surfactants. As noted above, conventional anionic surfactants typically cause inactivation of quaternary ammonium compounds by precipitating the quaternary ammonium compounds from solution. In sharp contrast, the "small" low molecular weight anionic surfactants with an HLB of 14 or above potentiate surfactant effectiveness and maintain biocidal effectiveness of quaternary ammonium compounds when associated with them in an aqueous medium, apparently through formation of one or more charge complexes. This unique coaction between components (i) and (ii) makes possible the provision of cleaning formulations with much better greasing cutting and wetting properties than that provided by either component used individually. And the disinfecting properties of the quaternary ammonium compound are left substantially intact and unimpaired. In this connection, some of the anionics useful pursuant to this invention may possibly belong to the group of solubilizers that are often used to enhance the solubility of nonionic and anionic surfactants in liquid products, especially when "ultra" type of liquids are desired. However, based on the phase behavior observed in the compositions of this invention, the behavior of the anionics is quite different from the general understanding of solubilizer.

In accordance with another of its embodiments, this invention provides a method of combating a pathological microorganism, which method comprises applying to the locus of such microorganism a biocidal amount of an aqueous composition of this invention. The result of such application is both biocidal action and cleansing.

Preferably, components (i) and (ii) are the only biocidal and surfactant components used in forming such compositions. If any other biocidal and/or surfactant is to be used, care should be taken to ensure that the beneficial properties made available by the practice of this invention are not materially impaired or depreciated by use of such other biocide or surfactant. Optionally, and preferably, one or more substances that are not biocides or surfactants, can be included in these compositions. Examples of such substances include dyes, fillers, perfumes, bleaches (e.g., sodium perborate, sodium percarbonate, etc.), abrasives, stabilizers, corrosion inhibitors, anti-dusting additives (e.g., high molecular weight alcohols), and thickeners. Desirable fillers include sodium carbonate, sodium bicarbonate, sodium sulfate, sodium tripolyphosphate, nitrilotriacetic acid or its sodium salts, ethylenediamine tetraacetic acid or its sodium salts, carboxymethoxysuccinic acid or its sodium salts, ethylenediamine disuccinic acid or its sodium salts, and like materials. Desirable abrasives include pumice, calcium carbonate, and silica.

Other embodiments and features of this invention will become still further apparent from the ensuing description, accompanying drawings, and appended claims.

FURTHER DETAILED DESCRIPTION

Component (i)

Figure 1:
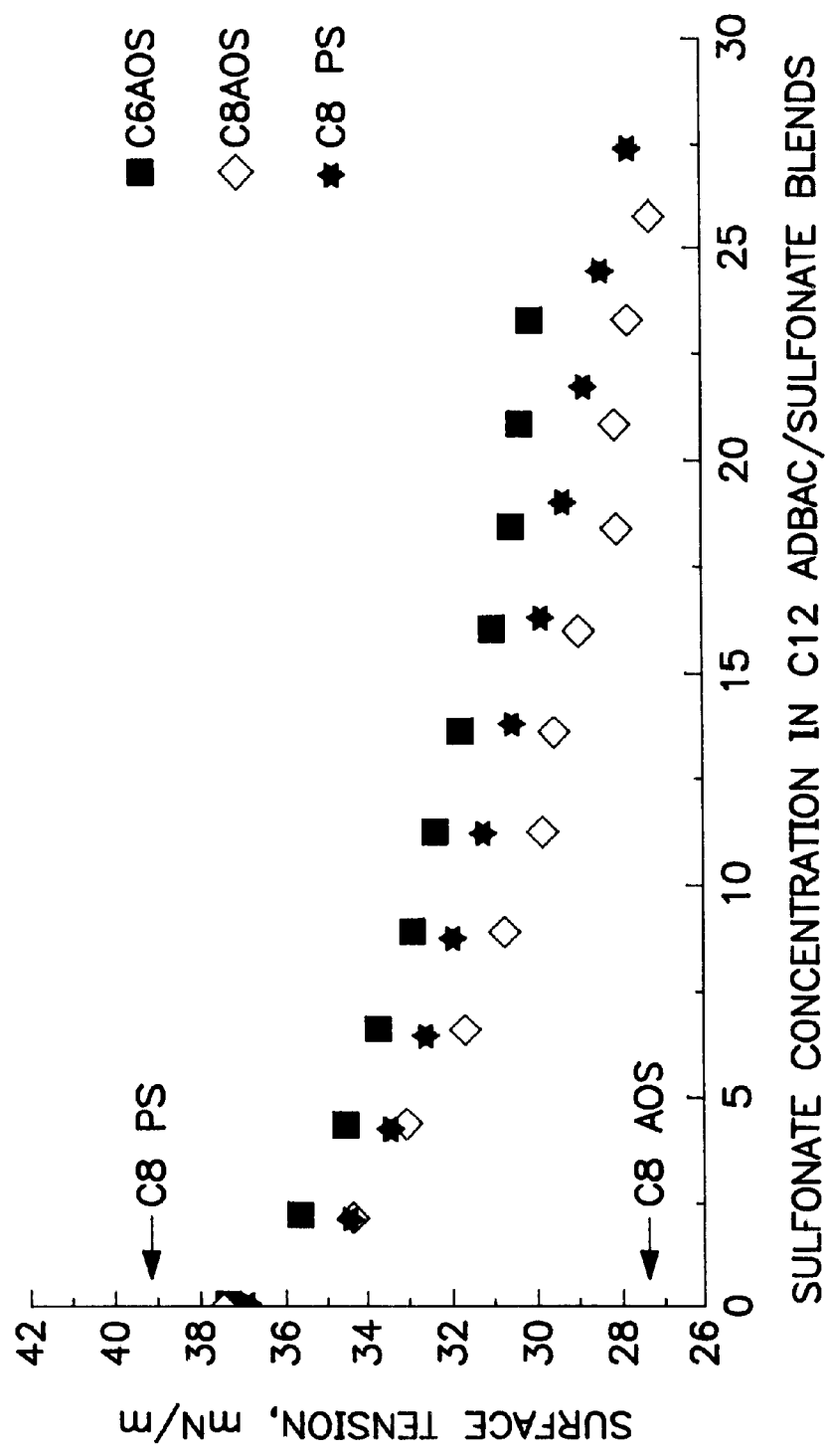
FIG. 1 is a visual presentation of surface tension data of various $C_{12}$ alkyldimethyl benzyl quaternary ammonium chloride/sulfonate formulations in water.

Component (i) used in forming the compositions of this invention is:

A) a water-soluble hydrocarbyldimethylbenzyl quaternary ammonium salt in which the hydrocarbyl group is (1) an alkyl group having in the range of from about 12 to about 16 carbon atoms or (2) an olefinically-unsaturated acyclic aliphatic group having up to 3 double bonds and in the range of from about 12 to about 16 carbon atoms, or (3) a mixture or combination of two or more of such compounds of A);

B) a water-soluble dihydrocarbyldimethyl quaternary ammonium salt in which the hydrocarbyl groups can be the same or different and in which the total number of carbon atoms in the two hydrocarbyl groups is in the range of about 16 to about 20, and each hydrocarbyl group is (1) an alkyl group having in the range of from 4 to about 16 carbon atoms or (2) an olefinically-unsaturated acyclic aliphatic group having up to 3 double bonds and in the range of from 4 to about 16 carbon atoms, or (3) a mixture or combination of two or more of such compounds of B); or C) a mixture or combination of one or more compounds of A) and one or more compounds of B).

When A) is a mixture or combination of such specified quaternary ammonium salt components, the average number of carbon atoms in the alkyl and/or olefinically-unsaturated acyclic aliphatic group of the components in the mixture is in the range of from about 12 to about 16 carbon atoms. Similarly when B) is a mixture or combination of such specified quaternary ammonium salt components, the average total number of carbon atoms in the two hydrocarbyl groups of the components in the mixture is in the range of from about 16 to about 20 carbon atoms.

When a hydrocarbyl group of such compounds is olefinically unsaturated and has more than one olefinic double bond, the double bonds should not be consecutively disposed (i.e., —CH=C=CH—) but rather should be conjugated double bonds (i.e., —CH=CH—CH=CH—) or should be spaced farther apart (e.g., —CH=CH—CH$_2$—

CH=CH—). The hydrocarbyl group, whether saturated (i.e., alkyl) or olefinically-unsaturated, it preferably is either a linear primary aliphatic group or a substantially linear primary aliphatic group with some methyl and/or ethyl branching on the chain, i.e., such branching should not impart to the quaternary ammonium compound properties which differ materially from the properties of the corresponding quaternary ammonium compound in which the aliphatic group is free of any branching. The quaternary ammonium salt is preferably a chloride or bromide, but quaternary ammonium salts in which the anion is iodide, sulfate, methylsulfate, or a like counter ion can also be used.

Thus, the water-soluble quaternary ammonium salt used pursuant to this invention can be represented by the formula:

$$R^1R^2(CH_3)_2N^{\oplus}X^{\ominus}$$

where $R^1$ is a saturated or olefinically-unsaturated acyclic aliphatic hydrocarbyl group, $R^2$ is a saturated or olefinically unsaturated acyclic aliphatic hydrocarbyl group, or a benzyl or alkyl-substituted benzyl group, and X is an anion, with the provisos that (a) if $R^2$ is a benzyl or alkyl-substituted benzyl group, $R^1$ has in the range of (or an average in the range of) about 12 to about 16 carbon atoms, and (b) if $R^1$ and $R^2$ are saturated or olefinically-unsaturated acyclic aliphatic hydrocarbyl groups, they can be the same or different, and each can have in the range of 4 to about 16 carbon atoms as long as the total number of carbon atoms in these two groups is in the range of (or is an average in the range of) about 16 to about 20 carbon atoms.

A few examples of the benzyl type compounds are dodecyldimethyl benzyl ammonium chloride, tridecyldimethyl benzyl ammonium chloride, tetradecyldimethyl benzyl ammonium chloride, pentadecyldimethyl benzyl ammonium chloride, hexadecyldimethyl benzyl ammonium chloride, dodecenyldimethyl benzyl ammonium chloride, tridecenyldimethyl benzyl ammonium chloride, tetradecenyldimethyl benzyl ammonium chloride, pentadecenyldimethyl benzyl ammonium chloride, hexadecenyldimethyl benzyl ammonium chloride, a mixture of dodecyl- and tetradecyldimethyl benzyl ammonium chlorides, a mixture of dodecyl-, tetradecyl-, and hexadecyldimethyl benzyl ammonium chlorides, a mixture of dodecyl-, tetradecyl-, hexadecyl-, and octadecyldimethyl benzyl ammonium chlorides having an average of about 14 carbon atoms in the molecule, a mixture of decyl-, dodecyl-, and tetradecyldimethyl benzyl ammonium chlorides having an average of about 12 carbon atoms in the molecule, a mixture of dodecyl- and dodecenyldimethyl benzyl ammonium chlorides, the bromide analogs of all of the foregoing, and analogous quaternary ammonium compounds of this type.

Illustrative of the dihydrocarbyl-type of quaternary ammonium compounds used pursuant to this invention are (butyl)(dodecyl)dimethylammonium chloride, (hexyl)(decyl)dimethylammonium chloride, (hexyl)(undecyl)dimethylammonium chloride, dioctyldimethylammonium chloride, dinonyldimethylammonium chloride, didecyldimethylammonium chloride, (octyl)(decyl)dimethylammonium chloride, (octyl)(undecyl)dimethylammonium chloride, (octyl)(dodecyl)dimethyl-ammonium chloride, (hexyl)(tridecyl)dimethylammonium chloride, (hexyl)(tetradecyl)dimethyl-ammonium chloride, (octyl)(7-methylnonyl)dimethylammonium chloride, di(3,4-dimethyloctyl)dimethylammonium chloride, di(4-octenyl)dimethylammonium chloride, di(8-nonenyl)dimethylammonium chloride, di(5-decenyl)dimethylammonium chloride, (butyl)(2-hexadecenyl)dimethylammonium chloride, (octenyl)(octyl) dimethylammonium chloride, the bromide analogs of all of the foregoing, and analogous quaternary ammonium compounds of this type.

Methods for the preparation of quaternary ammonium compounds are well known and published in the literature. Many are available on the open market as articles of commerce.

Component (ii)

Among suitable surfactants for use as component (ii) are alpha-olefin sulfonates, internal olefin sulfonates, paraffin sulfonates, aliphatic carboxylates, aliphatic phosphonates, aliphatic nitrates, and alkyl sulfates, which have an HLB of 14 or above. Examples of such surfactant types can be found in *McCutcheon's Emulsifiers and Detergents*, North American Edition, and International Edition, 1998 Annuals. In situations where the HLB of a given candidate for use as component (ii) is not already specified, the HLB can be calculated using the method described by J. T. Davies, *Proc. 2nd Int. Congr. Surf Act., London*, Volume 1, page 426. Also see P. Becher, *Surfactants in Solution*, Volume 3, K. L. Mittal, Ed., Plenum, New York, 1984; *J. Disp. Sci. & Tech*, 1984, 5, 81. It will be noted that surfactants meeting the HLB requirement of 14 or above have relatively small molecular structures as compared to conventional widely-used surfactants.

One type of highly preferred of component (ii), the second ingredient used in forming the compositions of this invention, is at least one water-soluble alkane sulfonic acid, or ester or salt thereof, (sometimes collectively referred to herein as "AOS"). Preferably the alkane portion of the molecule is a linear or substantially linear alkyl group having in the range of about 2 to about 8 carbon atoms. Such materials are typically formed by the sulfonation of alpha-olefin hydrocarbons with sulfur trioxide often using a falling film reactor.

The following Examples are presented to illustrate this invention and advantages achievable by the practice of this invention. They do not limit its scope, however. The accompanying Drawings depict results obtained in these Examples. The acronym, ADBAC, is used in the Examples and in the Drawings to denote alkyldimethyl benzyl ammonium chloride.

EXAMPLES

In the conduct of the experimental work described below, a Kruss 665 Dosimat was used for surface tension measurements, and a Kruss Model DVT-10 drop volume tensiometer was used for the measurements of dynamic interfacial tension. Distilled water was used in all the dynamic surface tension and interfacial tension measurements. Mineral oil, USP grade from J. T. Baker Co. was used as the oil phase.

The alkyldimethyl benzyl ammonium chlorides were prepared by reacting alkyldimethyl-amine with benzyl chloride in water. The C12 ADBAC was purified through recrystallized in ethylacetate. The C16 ADBAC was purified through recrystallization in water.

Contact angle measurements were conducted on a glass slide coated with a thin layer of Dow Corning high vacuum grease.

The 1-hexene sulfonate (C6 AOS) and 1-octene sulfonates (C8 AOS) were prepared through direct sulfonation of 1-hexene and 1-octene, respectively. The paraffin sulfonate (C8 PS) was prepared using bisulfite addition of 1-octene, followed by oxidation. According to NMR analysis, the C8 PS is a mixture of 52% mono-sulfonate and 48% of disulfonate. All the samples were deoiled with the exception of the xylene sulfonate. For the $C_6$ AOS (with an undetermined mixture of alkene, alkane, and hydroxy species present in the sulfonate structure), the calculated HLB ranges from 15.96 to 16.10, the variation coming from the absence or presence of the free —OH group. A similar calculation for the $C_8$ AOS gives a range of values of 14.20 to 16.10. The C8 PS likewise has an HLB above 14.

In FIG. 1 are plotted dynamic surface tension data vs. wt % of sulfonates in C12 ADBAC/sulfonate blends. The sum of C12 ADBAC and sulfonate in all the blends was kept constant at 1 wt %. The sulfonate contents in the blends ranged from 0 to around 25 wt %. It was noted that the solutions turned turbid when the sulfonate content exceeded this range. The solution turns clear again when the sulfonate content approached 90 wt %. The dynamic surface tension given in FIG. 1 were generated at a 50 mL/hr air feeding rate. Virtually the same values were obtained at a much slower feeding rate of 200 mL/hr. The dynamic surface tension of the sulfonates by themselves are also shown on FIG. 1 for reference purpose. FIG. 1 shows that in general, each of the sulfonates used pursuant to this invention were effective in reducing the dynamic surface tension of the C12 ADBAC. The effectiveness in surface tension reduction can be arranged in the decreasing order of C8 AOS>C8 PS>C6 AOS. In all cases, at the concentration just below that at which the aqueous mixture becomes turbid or cloudy, the dynamic surface tension attained by the blends were lower than any of the components by themselves. This synergism is more profound when the concentrations of the blends were reduced from 1 wt % to 0.1 wt %.

Figure 2:
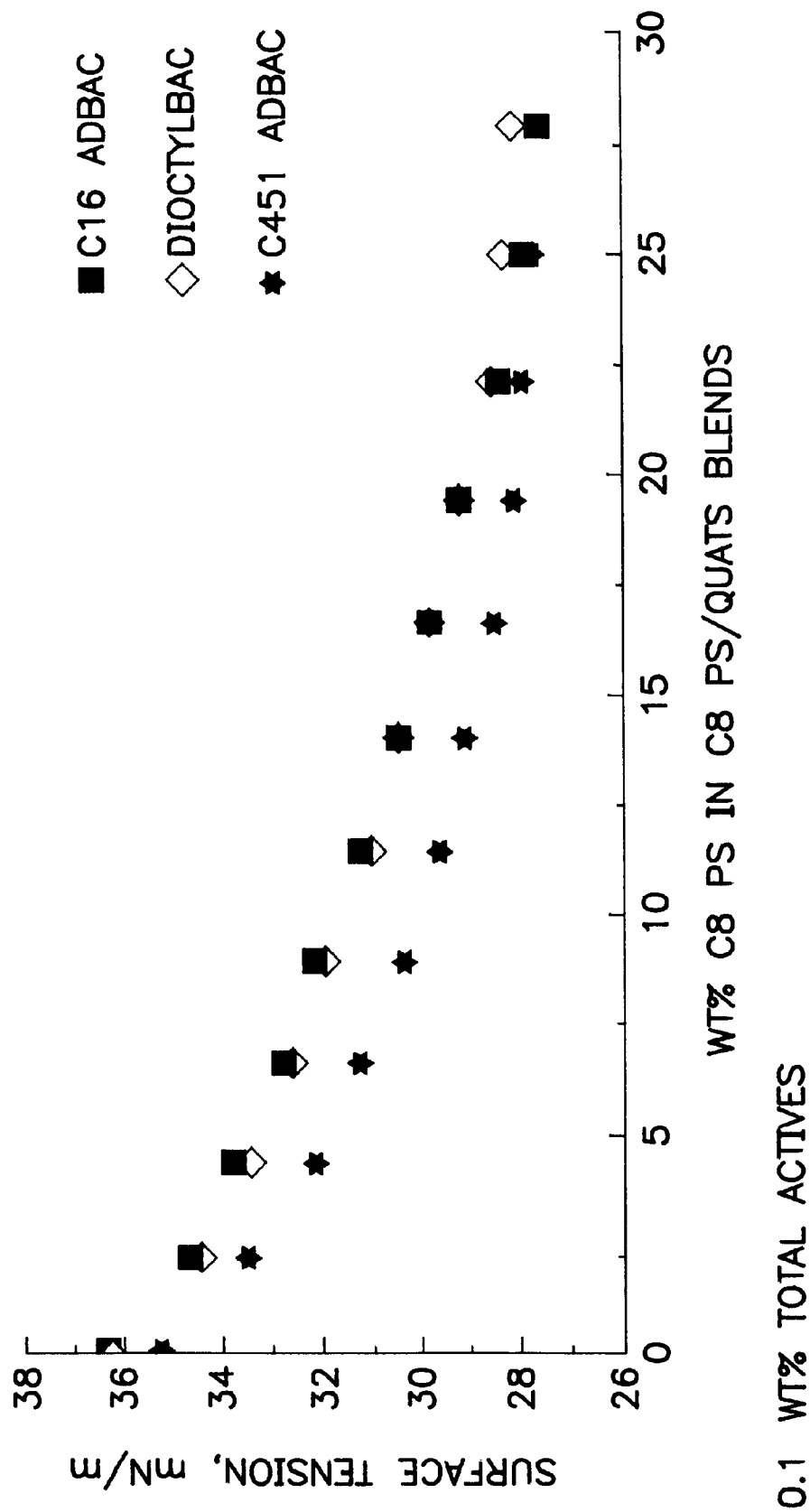
FIG. 2 is a visual presentation of surface tension data of various $C_8$ paraffin sulfonate/alkyldimethyl benzyl quaternary ammonium chloride formulations in water.

FIG. 2 presents plots of dynamic surface tension vs. wt % of sulfonates in various blends with three different quaternary ammonium chlorides: (1) C16 ADBAC, (2) DIOCTYLBAC (di(octyl)(methyl) benzyl ammonium chloride), and (3) C451 ADBAC (40 wt % $C_{12}$, 50 wt % $C_{14}$, and 10 wt % $C_{16}$ alkyldimethyl benzyl ammonium chlorides). FIG. 2 clearly shows that the surface tension reduction by the incorporation of suitable anionics is not limited to the C12 ADBAC. The surface tension of all three quats when used alone is around 34–37 mN/m, which supports the view that germicidal quats by themselves do not have good wetting properties.

Figure 3:
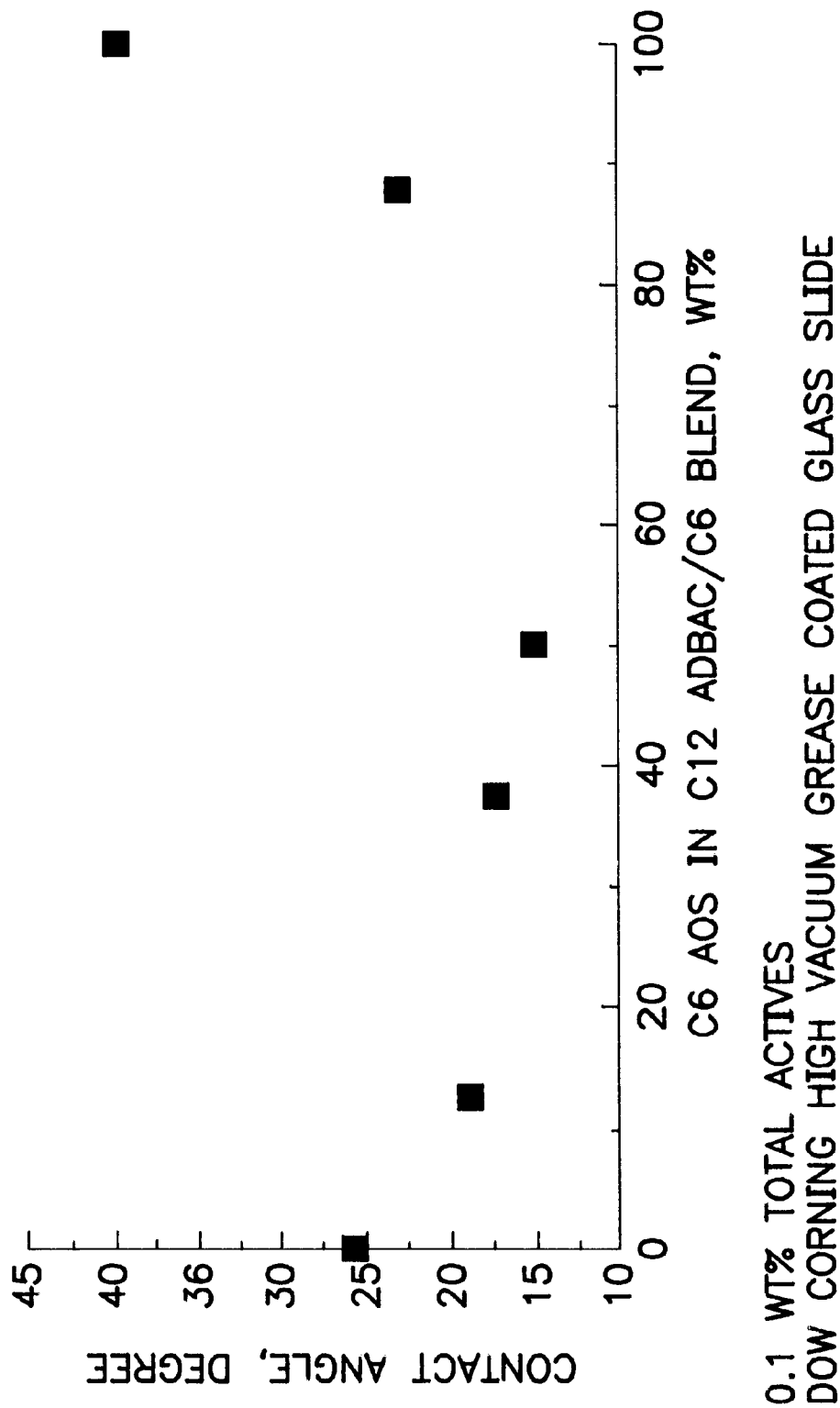
FIG. 3 is a visual presentation of contact angle data of various $C_{12}$ alkyldimethyl benzyl quaternary ammonium chloride/$C_6$ AOS formulations in water.

Although, it is generally accepted that lower surface tensions correspond to lower contact angles, this was confirmed by conducting separate contact angle determinations. A glass slide coated with Dow Corning high vacuum grease was used as the substrate. Small (0.01 mL) droplets of quat/C6 AOS were placed on the substrate for contact angle measurements. The data is shown in FIG. 3. It is clear from the data that lower contact angles did in fact result from the incorporation of suitable anionics pursuant to this invention, in this case, C6 AOS.

Figure 5:
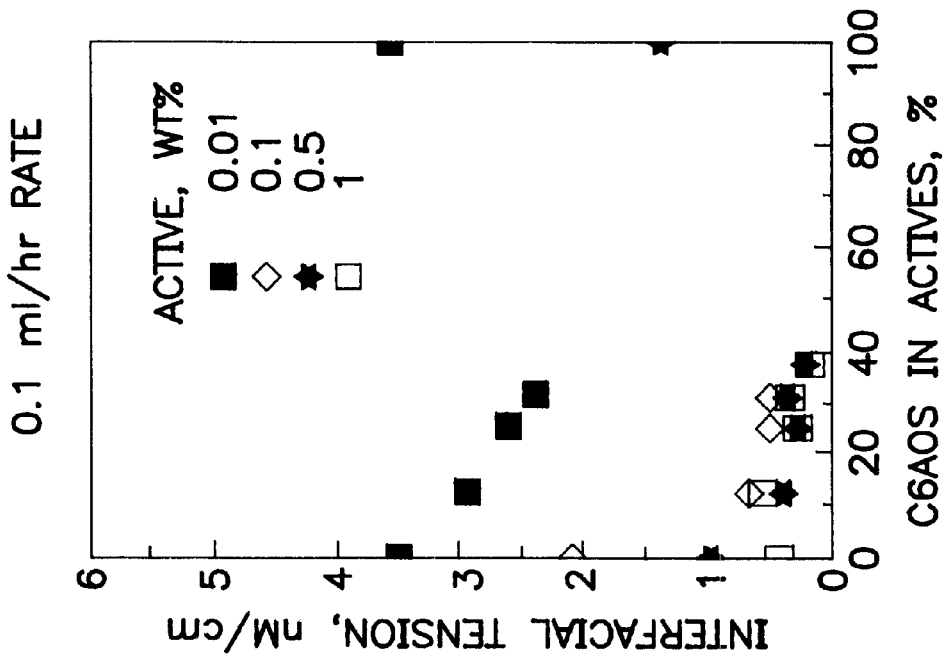
FIGS. 4 and 5 depict interfacial tension between mineral oil and $C_{12}$ alkyldimethyl benzyl quaternary ammonium chloride/$C_6$ AOS formulations at 1 and 0.1 milliliter per hour rates of oil addition, respectively.
Figure 4:
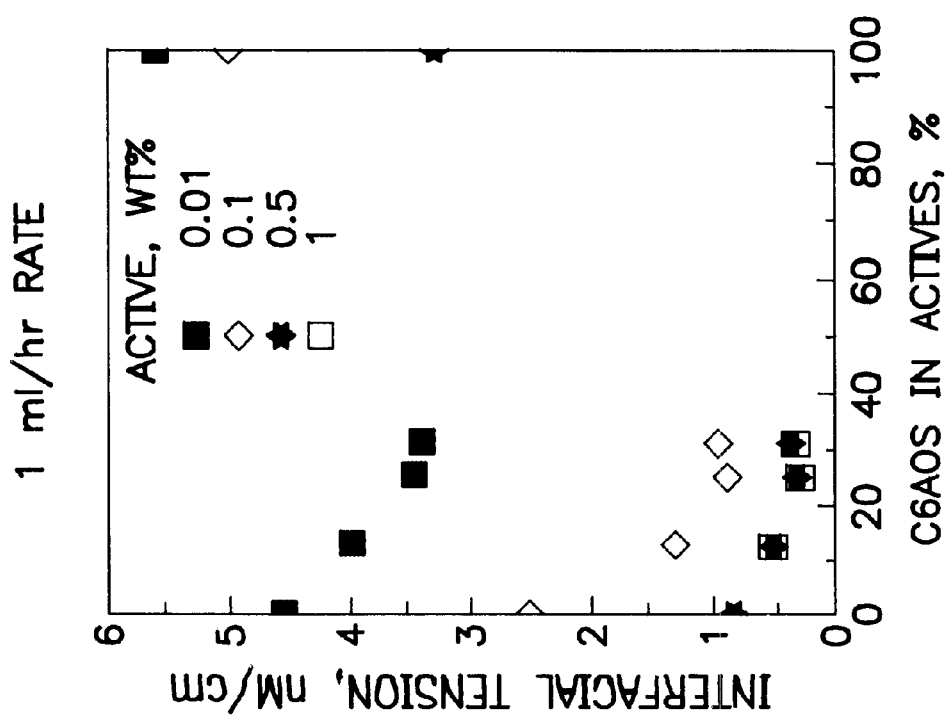

FIGS. 4 & 5 are the results of dynamic interfacial tension between a mineral oil and various C6 AOS/C12 ADBAC blends. The dynamic interfacial tensions were plotted against the wt % of C6AOS in C6 AOS/C12 ADBAC blends with total actives (sulfonate plus C12 ADBAC) of 0.01, 0.1, 0.5, and 1.0 wt. %, respectively. Only the blends that are clear were used for measurements. The data also shows that the dynamic interfacial tension of C12 ADBAC is reduced in the presence of C6AOS. The net benefit of adding C6AOS in a C12 ADBAC system in more profound in low concentrations than that in the cases of higher total concentration. FIG. 4 was generated with an mineral oil feeding rate of 1 mL/hr, and FIG. 5 was generated with an oil feeding rate of 0.1 mL/hr. The data indicates that dynamic interfacial tension is more sensitive to feeding rate for systems of low total actives.

Figure 7:
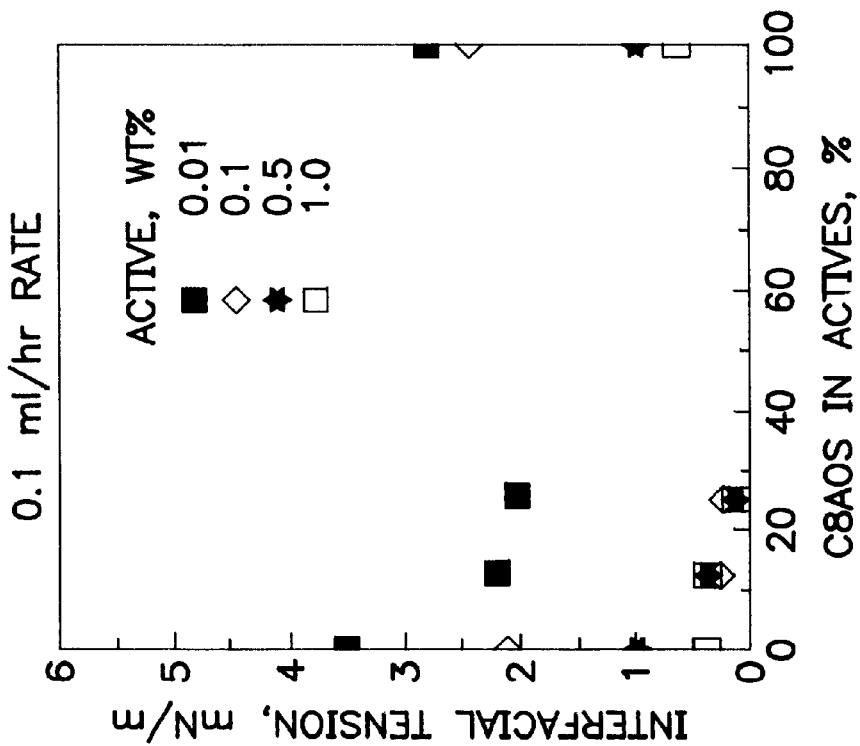
FIGS. 6 and 7 depict interfacial tension between mineral oil and $C_{12}$ alkyldimethyl benzyl quaternary ammonium chloride/$C_8$ AOS formulations at 1 and 0.1 milliliter per hour rates of oil addition, respectively.
Figure 6:
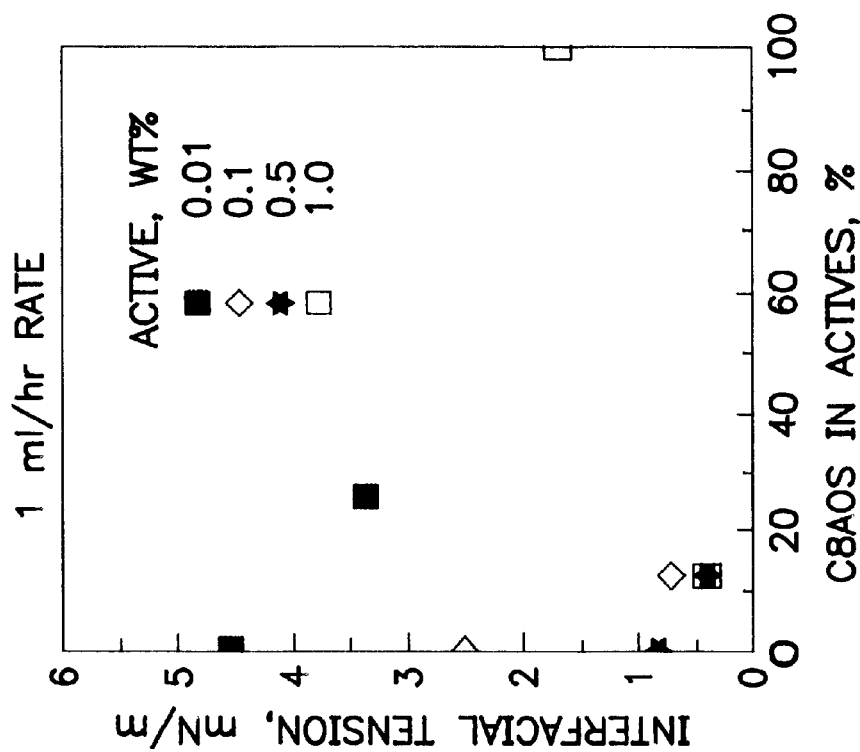
Figure 9:
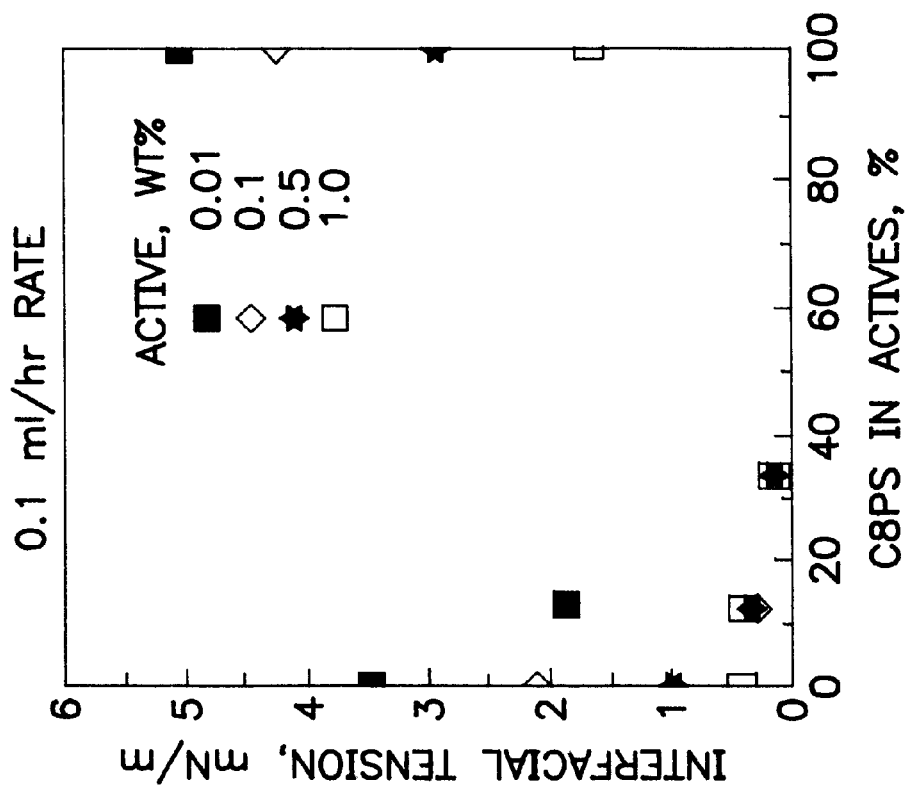
FIGS. 8 and 9 depict interfacial tension between mineral oil and $C_{12}$ alkyldimethyl benzyl quaternary ammonium chloride/$C_8$ paraffin sulfonate formulations at 1 and 0.1 milliliter per hour rates of oil addition, respectively.
Figure 8:
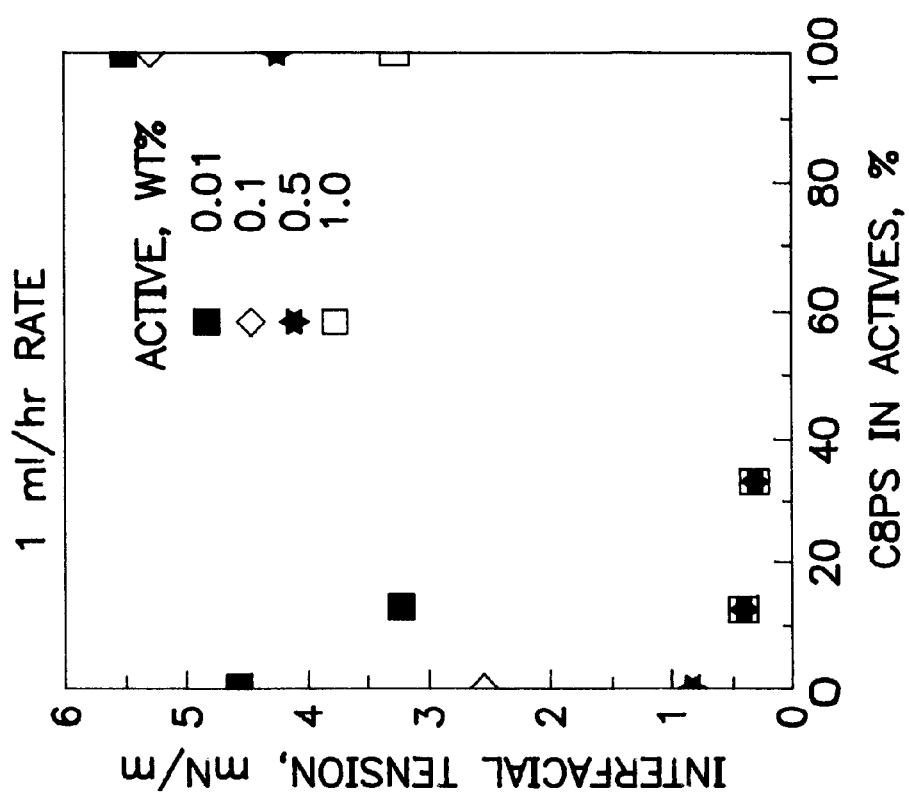

FIGS. 6 & 7 are plots of dynamic interfacial tensions between a mineral oil and various C8 AOS/C12 ADBAC blends, and FIGS. 8 & 9 show the results of dynamic interfacial tension measurements between mineral oil and C8 PS. All the data show that dynamic interfacial tension reduction is attainable by the incorporation of low molecular weight anionics.

Samples of 26 wt % of C6 AOS and C8 AOS were submitted to ViroMED Laboratories, Inc. to test biocidal efficacy following an AOAC approved method (*Escherichia coli* ATCC 11229). Preliminary efficacy testing results showed a 99.9% reduction in count of the number of living organisms.

It is to be understood that the components referred to by chemical name or formula anywhere in the specification or claims hereof, whether referred to in the singular or plural, are identified as they exist prior to coming into contact with another substance referred to by chemical name or chemical type (e.g., another component, solvent, or etc.). It matters not what chemical changes, transformations and/or reactions, if any, take place in the resulting mixture or solution or formulation as such changes, transformations and/or reactions (e.g., solvation, ionization, complex formation, or etc.) are the natural result of bringing the specified reactants and/or components together under the conditions called for pursuant to this disclosure. Thus, the components are identified as ingredients to be brought together in connection with forming a desired mixture or in forming a preliminary mixture to be used in forming a desired formulation or product mixture. Even though the claims hereinafter may refer to substances, components and/or ingredients in the present tense ("comprises," "is," etc.), the reference is to the substance, component or ingredient as it existed at the time just before it was first contacted, blended or mixed with one or more other substances, components and/or ingredients in accordance with the present disclosure, and with the application of common sense.

Each and every patent or other publication referred to in any portion of this specification is incorporated in toto into this disclosure by reference, as if fully set forth herein.

The invention is susceptible to considerable variation in its practice. Therefore, the foregoing description is not intended to limit, and should not be construed as limiting, the invention to the particular exemplification presented hereinabove. Rather, what is intended to be covered is as set forth on the ensuing claims and the equivalents thereof permitted as a matter of law.

That which is claimed is:

1. A cleaning and biocidal composition for use in aqueous media, said composition comprising:

i) at least one quaternary ammonium compound having the formula:

$$R^1R^2(CH_3)_2N^{\oplus}X^{\ominus}$$

where $R^1$ is a saturated or olefinically-unsaturated acyclic aliphatic hydrocarbyl group, $R^2$ is a saturated or olefinically unsaturated acyclic aliphatic hydrocarbyl group, or a benzyl or $C_{1-2}$ alkyl-substituted benzyl group, and X is an anion, with the provisos that (a) if $R^2$ is a benzyl or $C_{1-2}$ alkyl-substituted benzyl group, $R^1$ has in the range of about 12 to about 16 carbon atoms, or an average in the range of about 12 to about 16 carbon atoms, and (b) if $R^1$ and $R^2$ are saturated or olefinically-unsaturated acyclic aliphatic hydrocarbyl groups. they can be the same or different, and each can have in the range of 4 to about 16 carbon atoms as long as the total number of carbon atoms in these two groups is in the range of about 16 to about 20 carbon atoms, or is an average in the range of about 16 to about 20 carbon atoms; and ii) at least one water-soluble alpha-olefin sulfonate, internal-olefin sulfonate or paraffin sulfonate surfactant having a hydrophile/lipophile balance of 14 or above; wherein the amount of (ii) is in the range of about 1 to about 50 wt % of the total weight of (i) and (ii).

2. A composition of claim 1 wherein the weight of (ii) is in the range of about 2 to about 30 wt % of the total weight of (i) and (ii).

3. A composition of claim 1 wherein the weight of (ii) is in the range of about 5 to about 25 wt % of the total weight of (i) and (ii).

4. A composition of claim 1 wherein said composition is in the form of a solid compositions.

5. A composition of claim 1 wherein (ii) is at least one alpha-olefin sulfonate.

6. A composition of claim 1 wherein (ii) is at least one paraffin sulfonate.

7. A composition of claim 1 wherein (ii) is at least one alpha-olefin sulfonate having in the range of about 6 to about 8 carbon atoms in the molecule.

8. A composition of claim 1 wherein (ii) is at least one paraffin sulfonate having about 8 carbon atoms in the molecule.

9. A non-turbid, liquid, cleaning/disinfecting composition formed by intimately mixing with an aqueous medium (i) at least one quaternary ammonium compound and (ii) at least one water-soluble alpha-olefin sulfonate, internal-olefin sulfonate or paraffin sulfonate surfactant having a hydrophile/lipophile balance of 14 or above in proportions such that the amount of (ii) mixed with said medium is in the range of about 1 to about 50 wt % of the total weight of (i) and (ii) mixed with said medium; said at least one quaternary ammonium compound having, before mixing with the water, the formula:

$$R^1R^2(CH_3)_2N^{\oplus}X^{\ominus}$$

where $R^1$ is a saturated or olefinically-unsaturated acyclic aliphatic hydrocarbyl group, $R^2$ is a saturated or olefinically unsaturated acyclic aliphatic hydrocarbyl group, or a benzyl or $C_{1-2}$ alkyl-substituted benzyl group, and X is an anion, with the provisos that (a) if $R^2$ is a benzyl or $C_{1-2}$ alkyl-substituted benzyl group, $R^1$ has in the range of about 12 to about 16 carbon atoms, or average in the range of about 12 to about 16 carbon atoms, and (b) if $R^1$ and $R^2$ are saturated or olefinically-unsaturated acyclic aliphatic hydrocarbyl groups, they can be the same or different, and each can have in the range of 4 to about 16 carbon atoms as long as the total number of carbon atoms in these two groups is in the range of about 16 to about 20 carbon atoms, or is an average in the range of about 16 to about 20 carbon atoms.

10. A composition of claim 9 wherein the total concentration of components (i) and (ii) in the aqueous medium, whether blended therewith separately or as a preformed mixture and/or complex, is a cleansing and disinfecting quantity in the range of about 0.1 to about 5 wt % based on the total weight of water plus components (i) and (ii).

11. A composition of claim 10 wherein said cleansing and disinfecting quantity is in the range of about 0.4 to about 1 wt %, based on the total weight of water plus components (i) and (ii).

12. A composition of any of claims 1–4 or 9–11 wherein components (i) and (ii) are the only biocidal and surfactant components used in forming the composition.

13. A composition of claim 9 wherein (ii) is at least one alpha-olefin sulfonate.

14. A composition of claim 9 wherein (ii) is at least one paraffin sulfonate.

15. A composition of claim 9 wherein (ii) is at least one alpha-olefin sulfonate having in the range of about 6 to about 8 carbon atoms in the molecule.

16. A composition of claim 9 wherein (ii) is at least one paraffin sulfonate having about 8 carbon atoms in the molecule.

17. A method of combating a pathological microorganism and cleansing the locus thereof, which method comprises applying to the locus of such microorganism a biocidal and cleansing amount of a composition formed by intimately mixing with an aqueous medium (i) at least one quaternary ammonium compound and (ii) at least one water-soluble alpha-olefin sulfonate, internal-olefin sulfonate or paraffin sulfonate surfactant having a hydrophile/lipophile balance of 14 or above in proportions such that the amount of (ii) mixed with said medium is in the range of about 1 to about 50 wt % of the total weight of (i) and (ii) mixed with said medium; said at least one quaternary ammonium compound having, before mixing with the water, the formula:

$$R^1R^2(CH_3)_2N^{\oplus}X^{\ominus}$$

where $R^1$ is a saturated or olefinically-unsaturated acyclic aliphatic hydrocarbyl group, $R^2$ is a saturated or olefinically unsaturated acyclic aliphatic hydrocarbyl group, or a benzyl or $C_{1-2}$ alkyl-substituted benzyl group, and X is an anion, with the provisos that (a) if $R^2$ is a benzyl or $C_{1-2}$ alkyl-substituted benzyl group, $R^1$ has in the range of about 12 to about 16 carbon atoms, or an average in the range of about 12 to about 16 carbon atoms, and (b) if $R^1$ and $R^2$ are saturated or olefinically-unsaturated acyclic aliphatic hydrocarbyl groups, they can be the same or different, and each can have in the range of 4 to about 16 carbon atoms as long as the total number of carbon atoms in these two groups is in the range of about 16 to about 20 carbon atoms, or is an average in the range of about 16 to about 20 carbon atoms.

18. A method of claim 17 wherein the total concentration of components (i) and (ii) in the aqueous medium, whether blended therewith separately or as a preformed mixture and/or complex, is a cleansing and disinfecting quantity in the range of about 0.1 to about 5 wt % based on the total weight of water plus components (i) and (ii).

19. A method of claim 18 wherein said cleansing and disinfecting quantity is in the range of about 0.4 to about 1 wt %, based on the total weight of water plus components (i) and (ii).

20. A method of any of claims 17–19 wherein components (i) and (ii) are the only biocidal and surfactant components used in forming the composition.

21. A method of claim 17 wherein (ii) is at least one alpha-olefin sulfonate.

22. A method of claim 17 wherein (ii) is at least one paraffin sulfonate.

23. A method of claim 17 wherein (ii) is at least one alpha-olefin sulfonate having in the range of about 6 to about 8 carbon atoms in the molecule.

24. A method of claim 17 wherein (ii) is at least one paraffin sulfonate having about 8 carbon atoms in the molecule.

25. A method of enhancing the surfactant effectiveness of a biocidal quaternary ammonium compound without appreciably impairing the disinfecting properties of said compound, said method comprising mixing with an aqueous medium either separately or as a preformed mixture and/or complex:

i) at least one quaternary ammonium compound having the formula:

$$R^1R^2(CH_3)_2N^{\oplus}X^{\ominus}$$

where $R^1$ is a saturated or olefinically-unsaturated acyclic aliphatic hydrocarbyl group, $R^2$ is a saturated or olefinically unsaturated acyclic aliphatic hydrocarbyl group, or a benzyl or $C_{1-2}$ alkyl-substituted benzyl group, and X is an anion, with the provisos that (a) if $R^2$ is a benzyl or $C_{1-2}$ alkyl-substituted benzyl group, $R^1$ has in the range of about 12 to about 16 carbon atoms, or an average in the range of about 12 to about 16 carbon atoms, and (b) if $R^1$ and $R^2$ are saturated or olefinically-unsaturated acyclic aliphatic hydrocarbyl groups, they can be the same or different, and each can have in the range of 4 to about 16 carbon atoms as long as the total number of carbon atoms in these two groups is in the range of about 16 to about 20 carbon atoms, or is an average in the range of about 16 to about 20 carbon atoms; and ii) at least one water-soluble alpha-olefin sulfonate, internal-olefin sulfonate or paraffin sulfonate surfactant having a hydrophile/lipophile balance of 14 or above;

in proportions such that the amount of (ii) is in the range of about 1 to about 50 wt % of the total weight of (i) and (ii).

26. A method of claim 25 wherein the weight of (ii) is in the range of about 2 to about 30 wt % of the total weight of (i) and (ii).

27. A method of claim 26 wherein the weight of (ii) is in the range of about 5 to about 25 wt % of the total weight of (i) and (ii).

28. A method of any of claims 25–27 wherein components i) and ii) whether as individual components or as a complex thereof are the only biocidal and surfactant components mixed with said aqueous medium.

29. A method of claim 25 wherein (ii) is at least one alpha-olefin sulfonate.

30. A method of claim 25 wherein (ii) is at least one paraffin sulfonate.

31. A method of claim 25 wherein (ii) is at least one alpha-olefin sulfonate having in the range of about 6 to about 8 carbon atoms in the molecule.

32. A method of claim 25 wherein (ii) is at least one paraffin sulfonate having about 8 carbon atoms in the molecule.

* * * * *